United States Patent [19]
Nilsen

[11] Patent Number: 6,117,631
[45] Date of Patent: Sep. 12, 2000

[54] DETECTION OF ANTIGENS VIA OLIGONUCLEOTIDE ANTIBODY CONJUGATES

[75] Inventor: Thor W. Nilsen, Haddonfield, N.J.

[73] Assignee: Polyprobe, Inc., Philadelphia, Pa.

[21] Appl. No.: 08/738,641

[22] Filed: Oct. 29, 1996

[51] Int. Cl.[7] ........................ C12Q 1/68; A61K 39/395; C07H 19/00

[52] U.S. Cl. ............... 435/6; 424/1.49; 424/1.53; 424/130.1; 424/141.1; 435/7.1; 435/7.5; 435/7.9; 536/22.1; 536/23.1; 536/24.3; 536/25.3; 935/78; 935/88

[58] Field of Search ................... 424/1.49, 1.53, 424/130.1, 141.1, 178.1; 435/6, 7.1, 7.5, 7.9; 536/22.1, 23.1, 24.3, 24.31, 24.32, 25.3; 935/78, 88

[56] References Cited

U.S. PATENT DOCUMENTS

| | | | |
|---|---|---|---|
| 5,175,270 | 12/1992 | Nilsen et al. | 536/27 |
| 5,487,973 | 1/1996 | Nilsen et al. | 435/6 |
| 5,635,602 | 6/1997 | Cantor et al. | 530/390.1 |
| 5,656,731 | 8/1997 | Urdea | 530/390.1 |

OTHER PUBLICATIONS

Joerger et al, Analyte Detection with DNA–labeled antibodies and polymerase chain reaction, Clinical Chemistry, vol. 41, No. 9, pp. 1371–1377, Sep. 5, 1995.

Singh et al, Starburst dendrimers: enhanced performance and flexibility for immunoassays, Clinical Chemistry, vol. 40, No. 9, pp. 1845–1849, Sep. 1, 1994.

*Primary Examiner*—James C. Housel
*Assistant Examiner*—Rodney P. Swartz
*Attorney, Agent, or Firm*—Lerner, David, Littenberg, Krumholz & Mentlik, LLP

[57] ABSTRACT

The present invention provides a method of detecting antigens, which comprises immobilizing an antigen to a solid support and contacting the solid support with a means for hybridizing a labeled dendrimer to the antibody, through an oligonucleotide complexed thereto. A directly oligonucleotide labeled primary antibody or an oligonucleotide labeled secondary antibody may be employed, and a conventionally labeled dendrimer can subsequently be hybridized to the oligonucleotide through one or more of the outer arms of the dendrimer. The present invention offers the advantage over conventional methods of antigen detection by providing multiple label molecules per antigen, thereby enhancing the observed signal associated with the label.

18 Claims, 1 Drawing Sheet

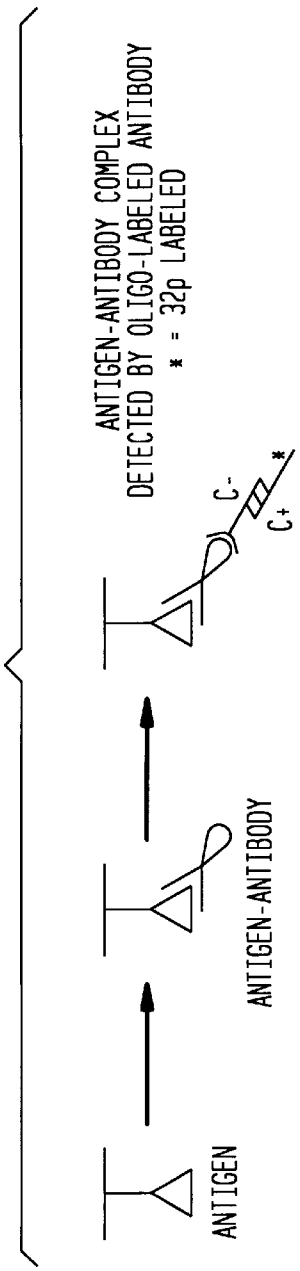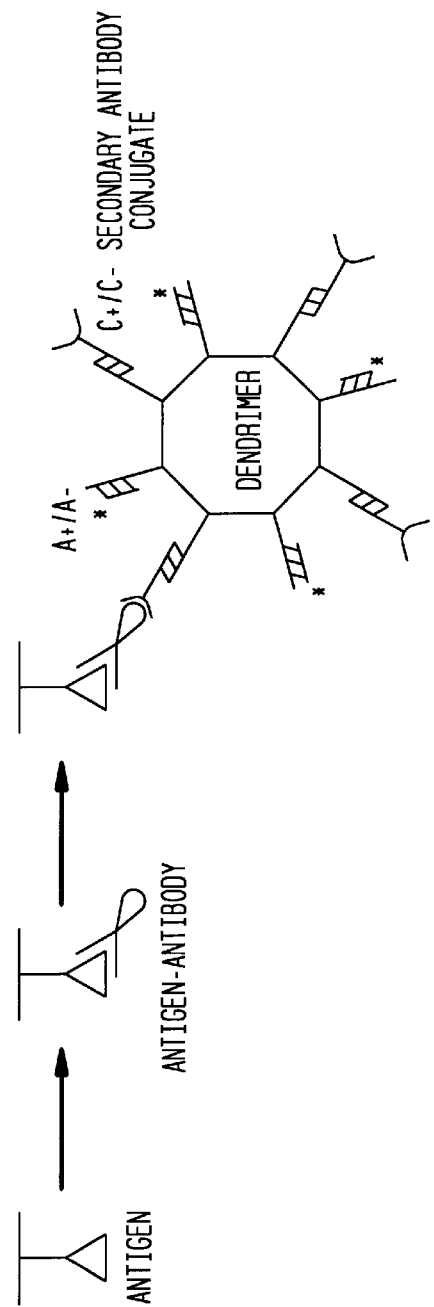

DETECTION OF ANTIGENS VIA OLIGONUCLEOTIDE ANTIBODY CONJUGATES

FIELD OF THE INVENTION

The present invention is directed to a method of detecting an antigen-antibody complex by the formation of immunodendrimers, i.e. oligonucleotide-antibody conjugates hybridized to labeled dendrimers. Immunodendrimers can amplify the signal observed in traditional methods by delivering multiple label molecules to a single antigen-antibody complex.

Several publications are referenced in this application, full citations of which are found in the text of the specification. These references describe the state-of-the-art to which this invention pertains, and are hereby incorporated herein by reference.

BACKGROUND OF THE INVENTION

The antigen-antibody interaction is a bimolecular association similar to an enzyme-substrate interaction, with the important distinction that it is a reversible process. The interactions between an antibody and an antigen are governed by various noncovalent interactions between the antigenic determinant, or epitope, of the antigen and the variable-region domain of the antibody molecule. The specificity of an antibody for an antigen has led to the development of a variety of immunologic assays which can be used to detect the presence of antibody or antigen. These assays have been instrumental in diagnosing diseases, monitoring the level of the humoral immune response, and identifying molecules of biological interest.

Antigens are routinely detected on membranes (Western blots) and in situ (immunohistochemistry, immunofluorescence, immunostaining, etc.) There are many variations on the available methods of detecting antigens, depending on the number and types of antibodies used, the label and the substrate. Independent of the variation, antigen detection essentially depends upon a specific antibody-antigen reaction forming an antibody-antigen complex.

The noncovalent interactions that comprise antigen-antibody binding include hydrogen bonds, and ionic, hydrophobic and van der Waals interactions, each of which is relatively weak in comparison to a covalent bond, and with each effective interaction operating over a very small distance. Therefore, a strong antigen-antibody interaction requires a large number of such associations, and a very tight fit between the antigen and antibody, owing to the high degree of specificity which is characteristic of antigen-antibody interactions.

The detection of the primary antibody-antigen complex has been demonstrated in numerous ways. Detection methods include directly labeled monoclonal antibody, wherein the label consists of an enzyme, e.g., alkaline phosphatase (AP), and Horseradish Peroxidase (HRP); a fluorochrome (a fluorescent compound), e.g., fluorescein, rhodamine, Texas Red, Cy-3, and Cy-5; a heavy metal chelate such as europium, lanthanum, yttrium, and gold; a radioactive isotope such as $^{125}I$, $^{131}I$, $^{3}H$, $^{14}C$, and $^{35}S$; or the label may be a secondary reporter, e.g., biotin, streptavidin, avidin, digoxigenin, or dinitrophenyl. Alternatively, detection methods may also include directly labeled polyclonal antibody, wherein the label may consist of the above-identified elements listed for monoclonal antibodies. Further, labeled secondary antibody which is polyclonal anti-first antibody, such as goat anti-mouse IgG-conjugate, may be used as a method of detection. Other detection methods include the use of labeled secondary reagent which is not necessarily an antibody, such as AP-streptavidin; labeled secondary antibody which is anti-conjugated epitope, such as HRP-goat-antifluorescein and AP-rabbit-anti-DNP; and unlabeled secondary antibody, detected with a labeled tertiary antibody or labeled tertiary component.

In extracts where the antigenic proteins represent only a tiny fraction of the total protein, the number and sizes of proteins with a particular epitope can be rapidly determined by Western blotting. Western blotting consists of electrophoretic transfer of an antigenic protein or proteins from a sodium dodecyl sulfate-polyacrylamide gel (SDS-PAGE) onto a nitrocellulose filter placed on one face of the gel, and as the protein is transferred, its position on the SDS-PAGE gel is preserved. The transferred protein binds tightly and non-covalently to the nitrocellulose, and can be exposed to a primary antibody that will bind to it. This bound primary antibody can then be bound by a secondary antibody containing a visualizable, covalently attached marker. If labeled specific antibody is not available, antigen-antibody complexes can be detected by adding a secondary anti-isotope antibody that is either radiolabeled or enzyme-labeled, and the band is visualized by autoradiography or substrate addition. Only those proteins with the epitope will be visualized in this manner, and if several proteins with different molecular weights have the epitope, each will be seen as a separate band on the nitrocellulose (S. Hockfield, et al., *Selected Methods for Antibody and Nucleic Acid Probes,* Cold Spring Harbor Laboratory Press, 1993, pp. 293–316).

Western blotting can identify either a given protein antigen or specific antibody. For example, Western blotting has been used to identify the envelope and core proteins of HIV and the antibodies to these components in the serum of HIV-infected individuals.

Immuno-PCR, a hybrid of PCR and immunoassay systems, combines the versatile molecular recognition of antibodies with the amplification potential of DNA replication. The technique involves the in situ assembly of the labeled DNA-antibody complex during the assay, creating variable stoichiometry in both the attachment of the DNA label, and the assembly of the components.

The procedural complexity of immuno-PCR has been reduced by the direct chemical attachment of DNA to analyte antibodies, whereby immobilized capture antibodies and a reporter antibody that carries a covalently attached DNA label are used, and the assay response is obtained by PCR of the DNA label and detection of the amplification products. This technique has been modified to develop an immuno-PCR sandwich assay for multiple analytes (see R. D. Joerger, et al., Clinical Chemistry, 1995, 41 (9): 1371–1377; E. R. Hendrickson, et al., Nucl. Acids Res., 1995, 23 (3): 522–529; and T. Sano, et al., Science, 1992, 258: 120–122).

However, immuno-PCR, albeit exhibiting enhanced sensitivity over traditional methods, is time consuming, complex and it does not lend itself to automation.

In order to detect a specific nucleic acid sequence, a highly specific probe DNA or RNA sequence (which is complementary to all or part of the sequence to be determined) is isolated, amplified by cloning, purified to homogeneity and labeled with a suitable marker. The purified, labeled DNA is added to a hybridization solution containing denatured nucleic acids (RNA or DNA) from a sample to be tested. The aqueous conditions of the hybridization solution are adjusted to allow nucleic acid hybridization or reannealing, thereby allowing the labeled molecules to hybridize with unlabeled, complementary sequence counterparts. Duplex formation can be monitored by digestion with single strand-specific nucleases (such as S1 nuclease). Recovery and quantitation of resistant, i.e., double-stranded, reannealed material provides a measure of the nucleic acid sequence tested for. The amount of hybridization is a function of the initial concentration of DNA and the time allowed for reannealing. Therefore, increased initial DNA concentrations can lead to substantially reduced hybridization times.

An example of the use of specific hybridization to detect sequences of oligonucleotides is that described by Southern, E., J. Mol. Biol. 98: 503, 1975. In this assay, a sample containing the DNA sequence to be detected is purified, digested with appropriate restriction endonucleases, and the fragments separated by gel electrophoresis. The fragments are then bound to a suitable solid support, such as nitrocellulose. This binding takes a minimum of 12 to 16 hours in the presence of a solution containing a relatively high concentration of sodium chloride. A labeled probe, complementary to the sequences to be determined, is then added to the nitrocellulose and allowed to hybridize for a period of 12 to 48 hours. After this period of time, the nitrocellulose must be washed under appropriate salt and temperature conditions, since otherwise the labeled probe will bind nonspecifically to both the membrane and to other non-homologous DNA sequences, leading to background "noise" or "false positives".

In a simplified version of the above-identified Southern hybridization assay, nucleic acid samples to be analyzed are "dotted" onto a solid support in an unfractionated state. The solid support is then probed as in the Southern hybridization assay, washed, and the amount of bound probe is quantitated.

However, there is no teaching in the prior art of using the above-identified techniques as a means to monitor the presence of an antigen of interest in a Western blot assay, without the additional requirement of PCR of the DNA label and detection of the amplification products.

U.S. Pat. Nos. 5,175,270 and 5,487,973 to Nilsen et al., herein incorporated by reference, are directed to dendrimers, a class of reagents for assaying nucleic acid sequences which are comprised of successive layers of polynucleotides, including a double-stranded waist and single-stranded, free arms at the molecule's ends, formed by hybridization of the arms to adjacent molecule arms. The outer layer polynucleotides are specific for the sequence to be identified, through their non-annealed, free, single-stranded arms.

It would be advantageous to develop a method of antibody detection which employs a Western blot technique with the oligonucleotide-antibody conjugates and the sensitivity of DNA dendrimers, without the necessity of performing PCR of the oligonucleotide label in order to detect the antigen-antibody complex.

OBJECTS AND SUMMARY OF THE INVENTION

It is an object of the present invention to provide a method of enhancing the sensitivity of detection of an antigen, which comprises immobilizing an antigen to a solid support, contacting the solid support with a means for attaching an immunodendrimer to the antigen, and quantitating the amount of antigen present by detecting the presence of a label attached to the immunodendrimer or an antibody complexed to the antigen-immunodendrimer complex, which method enables the attachment of multiple label molecules per antigen-antibody complex, thereby enhancing the observed signal for the complex.

The methods of the present invention provide a means for contacting an immobilized antigen with an antibody, primary or secondary, complexed to a dendrimer through an oligonucleotide attached to the antibody, thereby forming an immunodendrimer, which may be detected by means of a label attached to the dendrimer, or by contacting the solid support with an anti-dendrimer antibody.

Further, it is an object of the present invention to provide an oligonucleotide-antibody complex, wherein the oligonucleotide is labeled with $^{32}$P.

In an additional embodiment of the present invention, an oligonucleotide hybridized to first and second sequences of a dendrimer is provided to magnify the amount of label present for detection of the antigen-antibody complex, thereby enhancing the observed signal of the complex in comparison to standard techniques of antigen detection.

It is a further object of the invention to provide a method of detecting a labeled immunodendrimer, wherein the label is a fluorochrome, an enzyme, a heavy-metal chelate, a secondary reporter or a radioactive isotope.

These and other embodiments are disclosed or are obvious from the following detailed description.

BRIEF DESCRIPTION OF THE FIGURES

FIG. 1a shows a schematic representation of a $^{32}$P assay for detection of antigen-antibody complex, with a C(−) oligonucleotide conjugated secondary antibody labeled by a $^{32}$P labeled C(+) oligonucleotide; and FIG. 1b shows a schematic representation of $^{32}$P immunodendrimer assay, wherein C(+) arms of the dendrimer are conjugated to secondary antibody through a C(−) oligonucleotide, and the dendrimer is detected by a $^{32}$P labeled A(−) oligonucleotide hybridized to the A(+) arms of the dendrimer.

DETAILED DESCRIPTION OF THE INVENTION

The detection of antigen can be significantly enhanced via oligonucleotide-antibody conjugates hybridized to dendrimers, forming immunodendrimers. One of the key advantages of oligonucleotide-antibody conjugates is the facile labeling of the oligonucleotide moiety with radioactive phosphorus, biotin, digoxigenin and many other labels. Immunodendrimers can amplify the signal in traditional Western blots and in immunohistochemistry by delivering multiple label molecules to a single antigen-antibody complex.

In a traditional Western blot assay, antigen is labeled with a primary antibody, and the primary antibody is detected by a secondary antibody conjugated to a reporter molecule. The antigen-antibody complex is detected by analyzing the presence of each reporter molecule, which is limited to a single reporter molecule per antigen-antibody complex. If the antigen-antibody complex is present at very low concentrations, detection of the reporter molecule may be difficult and overshadowed by nonspecific interactions.

It has been surprisingly found that by using an antibody, either primary or secondary, capable of forming an antigen-antibody complex with an antigen of interest, the antibody being complexed with an oligonucleotide hybridized to a labeled DNA dendrimer, the sensitivity of detection of the antigen-antibody complex is substantially enhanced. The labeled DNA dendrimers, which serve as reporter molecules, permit a plurality of label molecules to be associated with a single antibody-antigen complex, thereby magnifying the detection signal by a factor equal to the number of labeled dendrimers complexed to the oligonucleotide.

In a preferred embodiment of the present invention, an antigen is immobilized to a solid support and contacted with a first antibody, thereby forming an antigen-antibody complex. The solid support is then contacted with a solution comprising an immunodendrimer, wherein the immunodendrimer comprises an anti-first antibody (or secondary antibody) having an oligonucleotide complexed thereto, and a labeled dendrimer hybridized to the oligonucleotide through one or more of the outermost layers of the dendrimer, i.e., the single-stranded ("arm") sequences of the dendrimer. The anti-first antibody of the immunodendrimer forms a complex with the first antibody, and the antigen is quantitated by detecting the presence of immunodendrimer.

Alternatively, an antigen may be detected by the method of the present invention by immobilizing an antigen to a solid support and contacting the solid support with a solution comprising an immunodendrimer, the immunodendrimer comprising an antibody capable of forming an antigen-antibody complex with the immobilized antigen, the antibody having an oligonucleotide complexed thereto, wherein a labeled dendrimer is hybridized to the oligonucleotide. The antigen is quantitated by detecting the presence of immunodendrimer.

In a further alternative embodiment of the present invention, an antigen may be detected by immobilizing the antigen to a solid support, and contacting the solid support with a solution comprising a first antibody, thereby forming an antigen-antibody complex. Subsequently, the solid support is contacted with a solution comprising an immunodendrimer, the immunodendrimer comprising an anti-first antibody (i.e., secondary antibody), having an oligonucleotide complexed thereto and a dendrimer hybridized to the oligonucleotide, wherein the anti-first antibody forms a complex with the first antibody. Thereafter, the solid support is contacted with a solution comprising a labeled tertiary anti-dendrimer antibody, wherein the tertiary antibody forms a complex with the dendrimer hybridized to the oligonucleotide, and the amount of antigen is quantitated by detecting the presence of labeled tertiary antibody.

In one embodiment of the present invention, the dendrimers may be labeled by standard techniques, i.e., by the use of fluorochromes (or fluorescent compounds), enzymes (e.g., alkaline phosphatase and horseradish peroxidase), heavy metal chelates, secondary reporters or radioactive isotopes.

Alternatively, the oligonucleotides used in the method of the present invention may be radiolabeled with radioactive phosphorus. In a preferred embodiment, the oligonucleotide is complexed at the 5' end to the antibody and the 3' end is labeled with $^{32}P$. The $^{32}P$ labeled oligonucleotide-antibody conjugates may be formed by conventional methods well known to those of ordinary skill in the art, e.g., by direct covalent linkage of the oligonucleotide to the antibody, wherein the antibody and the 5' amino-modified oligonucleotide are independently activated by means of separate heterobifunctional cross-linking agents (see E. Hendrickson, T. Hatfield Truby, R. Joerger, W. Majarian and R. Ebersole, Nucl. Acids Res., 1995, 23 (3): 522–529). Such oligonucleotide-antibody conjugates are very attractive labels due to the high energy of radioactive phosphorus and the relatively short half life. Further, the use of radioactive phosphorus allows for the use of a phosphorimager for detecting the amount of isotope in the antigen-antibody complex. Phosphorimagers yield quantitative information on the amount of isotope on a membrane, thereby improving the quantitation of the signal in a Western blot assay.

The DNA dendrimers used in the present invention are constructs comprising layers of DNA. The outermost layer of a given DNA dendrimer has single-stranded sequences ("arms") exposed to the surface which will hybridize with a predetermined nucleic acid sequence which is complexed to the antibody.

Further, the oligonucleotide may be hybridized to a first sequence of the dendrimer, and simultaneously, also hybridized to a second sequence of the dendrimer. Alternatively, multiple labeled dendrimers, each having sequences complementary to a different sequence of the oligonucleotide arms may be hybridized to a single oligonucleotide complexed to an antibody, thereby enabling a plurality of labeled molecules to be complexed to the antigen-antibody complex, and enhancing the detection of the signal associated with each antigen-antibody complex.

Each layer of the dendrimer molecule is composed of a particular class of matrix monomers. Matrix monomers have the property that sequential addition of monomers yields a three-dimensional DNA dendrimer matrix. The dendrimers are analogous to biological membranes in that they are selectively permeable to specific substances, for example, complementary DNA sequences complexed to an antibody.

Methods of making and using the DNA dendrimers used in the assay of the present invention are described in U.S. Pat. Nos. 5,175,270 and 5,487,973, herein incorporated by reference.

Additionally, a directly labeled primary antibody, monoclonal or polyclonal, conjugated to an oligonucleotide, which may be hybridized to a dendrimer, may be used in the method of the present invention. The dendrimer can be labeled by a secondary reporter, such as biotin, a fluorochrome, an enzyme, a heavy metal chelate or a radioactive isotope, and detected by standard methods. Alternatively, the dendrimer (or immunodendrimer) may be detected by contacting the solid support with a labeled anti-dendrimer antibody and using conventional methods to quantitate the amount of label present.

The antibodies used in the method of the present invention may be either monoclonal or polyclonal. Briefly, monoclonal antibodies are secreted by hybridomas, which are produced by fusion of an immortal cell (a myeloma cell) with an antibody-secreting cell (a lymphocyte) harvested from an immunized animal. The polyclonal response of an animal to an antigen or mixture thereof can thereby be broken down into its individual components through the single-cell cloning process involved in hybridoma production.

Additionally, an antibody which is an anti-conjugated hapten may also be used in the method of the present invention. Antibodies of this type are typically monoclonal, and recognize the particular hapten, such as dinitrophenol (DNP), when it is conjugated to, typically, a secondary antibody, such as goat anti-mouse.

Moreover, labeled secondary antibody which is polyclonal anti-first antibody may be used. Alternatively, unlabeled secondary antibody detected by a labeled tertiary anti-second antibody or a tertiary anti-dendrimer antibody (when a dendrimer which is complexed to an oligonucleotide attached to a bound secondary antibody is used) may be used in the present invention.

Methods of generating antibodies, both polyclonal and monoclonal, can be found in *Molecular Cloning, A Laboratory Manual,* 2nd Ed. by J. Sambrook, E. F. Fritsch and T. Maniatis (1989), Vol. 3, pp. 18.2–18.18, and *Selected Methods for Antibody and Nucleic Acid Probes,* by S. Hockfield et al. (1993), pp. 59–109.

The various permutations on the antibodies available for use in the method of the present invention will be obvious to one of ordinary skill in the art of immunology. The skilled artisan will recognize that regardless of the combinations of antibodies utilized, the method of the present invention may be universally employed to complex a dendrimer to an antibody for the detection of antigen.

Further, any conventional method of labeling dendrimers (or oligonucleotides) for use in the present invention may be employed. These methods include the use of enzymes, such as alkaline phosphatase and horseradish peroxidase, secondary reporters, such as biotin, with secondary reporter molecules complementary thereto, such as avidin, streptavidin, and anti-biotin antibodies, heavy metal chelates, such as gold, radioactive isotopes, i.e., $^{125}$I, $^{3}$H, $^{35}$S and $^{32}$P, and fluorochromes (fluorescent compounds), i.e., fluorescein and rhodamine.

Similarly, any method available for the detection of the above-identified labels may be employed in the method of the present invention, such as autoradiography, fluorography, phosphorimager and fluorimetry. The skilled artisan will recognize that each of the aforementioned permutations may be employed in the method of the present invention without departing from the spirit or scope thereof, and without the burden of undue experimentation.

The present invention is further described and illustrated in the following examples. Further objects of this invention, together with additional features contributing thereto and advantages accruing therefrom, will be apparent from the following examples of the invention. It will be appreciated that variations and modifications to the products and methods can be made by the skilled person without departing from the spirit or scope of the invention as defined in the appended claims.

EXAMPLES

Example 1

Amplification of Signal in Western Blot

Beta-galactosidase (Sigma) was serially 1:10 diluted and applied to a 4–20% SDS-PAGE gel (Novex). Monoclonal mouse anti-bgal (clone gal-13) was used as the primary antibody. Polyclonal rabbit anti-mouse-AP was used as the labeled secondary antibody in the traditional Western blot detection mode. Polyclonal goat anti-mouse antibody was conjugated to 5' NH$_3$-oligonucleotide by Synthetic Genetics. DNA dendrimers were obtained from Polyprobe Inc. and were labeled with biotin with the Rad-Free™ labeling system.

In a standard Western blot assay, serially diluted samples of Beta-galactosidase antigen were separated by SDS-PAGE, and the protein bands were transferred onto the nitrocellulose filter by using a semi-dry apparatus (Novex).

When the transfer of the proteins onto the nitrocellulose was complete, the nitrocellulose was separated from the SDS-PAGE gel, and soaked in a concentrated nonantigenic protein solution, i.e., blocking solution, e.g., 5% w/v non-fat dry milk. The protein in the solution binds nonspecifically to all of the areas on the nitrocellulose that have not already adsorbed protein from the SDS-PAGE gel, in an attempt to prevent the antibodies from binding nonspecifically to the nitrocellulose and increasing the probability that they will bind only to the immobilized antigen proteins. To further ensure that the antibodies do not bind nonspecifically to the nitrocellulose or to irrelevant proteins on the nitrocellulose, the antibodies were diluted in the nonantigenic protein solution before they were applied to the nitrocellulose.

The nitrocellulose was probed with diluted monoclonal mouse anti-Beta-galactosidase, and the membrane was washed sequentially in buffer (TBS/Tween 20, wherein TBS is Tris buffered saline, and Tween 20 is PEG (20) sorbitan monolaurate; the TBS/Tween 20 buffer consists of 50 mM Tris-HCl, pH 7.5, 150 mM NaCl and 0.1% Tween 20) at room temperature. The washing solution was discarded, and the membrane was probed with rabbit anti-mouse-AP. The antibody solution was removed, and the membrane was washed sequentially in TBS/Tween 20. Luminphos-530 was added, and the nitrocellulose was exposed to X-ray film.

The results are shown in FIG. 1A, wherein the lanes represent: (1) approximately 1 ug mouse anti-Beta galactosidase; (2) approximately 1 ug rabbit anti-mouse; (3) 1 ug Beta-galactosidase; (4) 100 ng Beta-galactosidase; and (5) 10 ng Beta-galactosidase.

In the assay of the present invention, serially diluted samples of Beta-galactosidase antigen (using the same dilution ratio used in the traditional Western assay described hereinabove) were separated by SDS-PAGE, and the protein bands were transferred onto the nitrocellulose filter.

When the transfer of the proteins onto the nitrocellulose was complete, the nitrocellulose was separated from the SDS-PAGE gel, and soaked in a concentrated nonantigenic protein solution, i.e., blocking solution, e.g., 5% w/v non-fat dry milk.

The nitrocellulose was probed with diluted monoclonal mouse anti-Beta-galactosidase, and the membrane was washed sequentially in TBS/Tween 20. The washing solution was discarded, and the membrane was probed with goat anti-mouse dendrimer. The membrane was washed sequentially in TBS/Tween 20, and the membrane was probed with streptavidin-AP. The antibody solution was removed, and the membrane was washed sequentially in TBS/Tween 20. Luminphous-530 was added, and the nitrocellulose was exposed to X-ray film.

The results are shown in FIG. 1B, wherein the lanes represent: (1) approximately 1 ug mouse anti-Beta galactosidase; (2) approximately 1 ug rabbit anti-mouse; (3) 1 ug Beta-galactosidase; (4) 100 ng Beta-galactosidase; and (5) 10 ng Beta-galactosidase.

The data clearly demonstrate superior sensitivity for the blot probed with DNA dendrimers.

Example 2

UP Western Assay

Beta-galactosidase (Sigma) was serially diluted (1:10) and applied to a 4–20% SDS-PAGE (NOVEX). Monoclonal mouse anti-bgal (clone gal-13) was the primary antibody; polyclonal goat anti-mouse antibody, conjugated to a 5' oligonucleotide by Synthetic Genetics (the C(−) oligonucleotide) was the secondary antibody; and 5'-$^{32}$P labeled C(+) oligonucleotide was the probe. Immunodendrimers were formed by combining approximately 100 ng C(−)-oligonucleotide of a C(−)-antibody conjugate (Synthetic Genetics), and 1 ug total 4-layer dendrimer in 100 ul TBS/Tween 20. The oligonucleotide was allowed to hybridize for at least 1 hour at 37° C.

In a $^{32}$P Western Assay, serially diluted samples of Beta-galactosidase were separated by SDS-PAGE and the protein bands were transferred onto a nitrocellulose filter.

When the transfer of the proteins onto the nitrocellulose was complete, the nitrocellulose was separated from the SDS-PAGE gel, and soaked in a concentrated nonantigenic protein solution, i.e., blocking solution, e.g., 5% w/v non-fat dry milk.

The nitrocellulose was probed with diluted monoclonal mouse anti-Beta-galactosidase, the membrane was washed sequentially in TBS/Tween 20, and the washing solution was discarded. $^{32}$P-C(+)-oligonucleotide was hybridized to C(−)-secondary antibody conjugate. The membrane was probed with the $^{32}$P-C(+)-oligonucleotide-C(−)-antibody conjugate, washed sequentially in TBS/Tween 20, and exposed to x-ray film. The results are shown in FIG. 2A, and the assay is shown schematically in FIG. 2C.

In comparison, the results of antigen detection by the method of the present invention, i.e., using an immunodendrimer and a $^{32}$P-labeled oligonucleotide probe are shown in FIG. 2B (shown schematically in FIG. 2D). Briefly, in a $^{32}$P Western Assay, serially diluted samples of Beta-galactosidase were separated by SDS-PAGE and transferred to nitrocellulose, as described hereinabove.

The nitrocellulose was probed with diluted monoclonal mouse anti-Beta-galactosidase, and the membrane was washed sequentially in TBS/Tween 20.

A four layer dendrimer, having C(+) oligonucleotide arms, complementary to the C(−) oligonucleotide complexed to the secondary antibody, and A(+) oligonucleotide arms (wherein the oligonucleotide arms designated A(+) and C(+) are different) was used as a probe. $^{32}$P-A(−)-oligonucleotide and C(−)-antibody conjugate were hybridized to a 4 layer dendrimer, with the 5'-$^{32}$P labeled A(−) oligonucleotide complementary to the A(+) arms of the immunodendrimer. The membrane was probed with the preannealed, labeled conjugate-dendrimer assembly, and the membrane was washed in TBS/Tween 20. The membrane was washed sequentially in TBS/Tween 20, and exposed to x-ray film.

The results clearly demonstrate the enhanced signal associated with the use of an immunodendrimer. $^{32}$P labeled oligonucleotide-antibody conjugates are very attractive labels due to the high energy of $^{32}$P and short half life. In addition, phosphorimagers may be used, as an alternative to x-ray detection, which are capable of yielding quantitative information on the amount of isotope on a Western blot, thereby improving the quantitation of Western blot assay.

Having thus described in detail certain preferred embodiments of the present invention, it is to be understood that the invention defined by the appended claims is not to be limited by particular details set forth in the above description, as many apparent variations thereof are possible without departing from the spirit or scope thereof.

What is claimed is:

1. A method of detecting an antigen comprising:
   immobilizing an antigen to a solid support;
   contacting the solid support with a first solution comprising a first antibody which binds to said immobilized antigen;
   contacting said solid support with a second solution comprising an immunodendrimer, said immunodendrimer comprising an anti-first antibody having an oligonucleotide complexed thereto and a labeled dendritic polynucleotide hybridized thereto, wherein the anti-first antibody binds to the first antibody;
   wherein said labeled dendritic polynucleotide comprises a plurality of matrix polynucleotide monomers bonded together by hybridization; each matrix polynucleotide monomer, prior to being hybridization bonded to other matrix polynucleotide monomers, having at least three single stranded hybridization regions, and in said dendritic polynucleotide each matrix polynucleotide monomer is hybridization bonded to at least one other matrix polynucleotide monomer at at least one such hybridization region and when hybridization bonded to more than one such hybridization region of the same matrix polynucleotide monomer, there is an intermediate region where the two monomers are not hybridization bonded; wherein each matrix polynucleotide monomer, prior to hybridization bonding has a linear, double stranded waist region having a first end and a second end, said first end terminating with two single stranded hybridization regions, each from a strand of the waist region, and said second end terminating with one or two single stranded hybridization regions, each from a strand of the waist region; and, the plurality of matrix polynucleotide monomers present does not exceed saturation of the labeled dendritic polynucleotide; and
   detecting the presence of said antigen directly by detecting said labeled immunodendrimer.

2. The method of claim 1, wherein said oligonucleotide is hybridized to a first single stranded hybridization arm of said labeled dendritic polynucleotide, and a second labeled oligonucleotide is hybridization to a second single stranded hybridization arm of said labeled dendritic polynucleotide.

3. The method of claim 1 wherein said oligonucleotide has a 3' and a 5' end, said oligonucleotide being complexed at said 5' end to said anti-first antibody, and said 3' end of said oligonucleotide being labeled with $^{32}$P.

4. The method of claim 3 wherein said oligonucleotide is hybridized to a first single stranded hybridization arm of said labeled dendritic polynucleotide, and a second labeled oligonucleotide is hybridized to a second single stranded hybridization arm of said labeled dendritic polynucleotide.

5. The method of claim 1 wherein said labeled dendritic polynucleotide is labeled with a first secondary reporter, and the amount of said immobilized antigen is detected by the addition of a second secondary reporter, complementary to said first secondary reporter and conjugated to a molecule selected from the group consisting of a fluorochrome, an enzyme, a heavy metal chelate, and a radioactive isotope.

6. The method of claim 5 wherein said first secondary reporter is biotin, and said second secondary reporter is selected from the group consisting of avidin, streptavidin, and anti-biotin antibody.

7. The method of claim 1 wherein said labeled dendritic polynucleotide is labeled with a molecule selected from the group consisting of a fluorochrome, and enzyme, a heavy metal chelate, and a radioactive isotope.

8. The method of claim 1 wherein said first antibody is monoclonal and said anti-first antibody is polyclonal.

9. A method of detecting an antigen, comprising:
   immobilizing an antigen to a solid support;
   contacting the solid support with a solution comprising an immunodendrimer, the immunodendrimer comprising an antibody which binds to the immobilized antigen, wherein said antibody has a oligonucleotide complexed thereto, said oligonucleotide having a labeled dendritic polynucleotide hybridized thereto;
   wherein said labeled dendritic polynucleotide comprises a plurality of matrix polynucleotide monomers bonded together by hybridization; each matrix polynucleotide monomer, prior to being hybridization bonded to other matrix polynucleotide monomers, having at least three single stranded hybridization regions, and in said dendritic polynucleotide each matrix polynucleotide monomer is hybridization bonded to at least one other matrix polynucleotide monomer at at least one such hybridization region and when hybridization bonded to more than one such hybridization region of the same matrix polynucleotide monomer, there is an intermediate region where the two monomers are not hybridization bonded; wherein each matrix polynucleotide monomer, prior to hybridization bonding has a linear, double stranded waist region having a first end and a second end, said first end terminating with two single stranded hybridization regions, each from a strand of the waist region, and said second end terminating with one or two single stranded hybridization regions, each from a strand of the waist region; and, the plurality of matrix polynucleotide monomers present does not exceed saturation of the labeled dendritic polynucleotide; and detecting the presence of said antigen directly by detecting said labeled immunodendrimer.

10. The method of claim 9 wherein said labeled dendritic polynucleotide is labeled with a molecule selected from the group consisting of a fluorochrome, an enzyme, a heavy metal chelate, and a radioactive isotope.

11. The method of claim 9 wherein said antibody is monoclonal.

12. The method of claim 9 wherein said oligonucleotide is hybridized to a first single stranded hybridization arm of said dendritic polynucleotide, and a labeled oligonucleotide is hybridized to a second single stranded hybridization arm of said dendritic polynucleotide.

13. The method of claim 9 wherein said oligonucleotide has a 3' and a 5' end, said oligonucleotide being complexed at said 5' end to said antibody, and said 3' end of said oligonucleotide being labeled with $^{32}$P.

14. The method of claim 13, wherein said oligonucleotide is hybridized to a first single stranded hybridization arm of said dendritic polynucleotide, and a labeled oligonucleotide is hybridized to a second single stranded hybridization arm of said dendritic polynucleotide.

15. The method of claim 9 wherein said labeled dendritic polynucleotide is labeled with a first secondary reporter, and the amount of said immobilized antigen is detected by the addition of a second secondary reporter, complementary to said first secondary reporter and conjugated to a molecule selected from the group consisting of a fluorochrome, an enzyme, a heavy metal chelate, and a radioactive isotope.

16. The method of claim 15 wherein said first secondary reporter is biotin, and said second secondary reporter is selected from the group consisting of avidin, streptavidin, and anti-biotin antibody.

17. A method of detecting an antigen comprising:

immobilizing an antigen to a solid support;

contacting the solid support with a first solution comprising a first antibody which binds to said immobilized antigen;

contacting the solid support with a second solution comprising an immunodendrimer, said immunodendrimer comprising an anti-first antibody which binds to said first antibody, said anti-first antibody having an oligonucleotide complexed thereto, wherein a dendritic polynucleotide is hybridized to said oligonucleotide;

wherein said labeled dendritic polynucleotide comprises a plurality of matrix polynucleotide monomers bonded together by hybridization; each matrix polynucleotide monomer, prior to being hybridization bonded to other matrix polynucleotide monomers, having at least three single stranded hybridization regions, and in said dendritic polynucleotide each matrix polynucleotide monomer is hybridization bonded to at least one other matrix polynucleotide monomer at at least one such hybridization region and when hybridization bonded to more than one such hybridization region of the same matrix polynucleotide monomer, there is an intermediate region where the two monomers are not hybridization bonded; wherein each matrix polynucleotide monomer, prior to hybridization bonding has a linear, double stranded waist region having a first end and a second end, said first end terminating with two single stranded hybridization regions, each from a strand of the waist region, and said second end terminating with one or two single stranded hybridization regions, each from a strand of the waist region; and, the plurality of matrix polynucleotide monomers present does not exceed saturation of the labeled dendritic polynucleotide;

contacting said solid support with a third solution comprising a labeled tertiary anti-dendritic polynucleotide antibody, wherein said labeled tertiary anti-dendritic polynucleotide antibody binds to said immunodendrimer; and detecting the presence of said antigen directly by detecting said labeled immunodendrimer.

18. The method of claim 17 wherein said labeled tertiary antibody is labeled with a molecule selected from the group consisting of a fluorochrome, an enzyme, a heavy metal chelate, a secondary reporter, and a radioactive isotope.

* * * * *

UNITED STATES PATENT AND TRADEMARK OFFICE
CERTIFICATE OF CORRECTION

PATENT NO. : 6,117,631
DATED : September 12, 2000
INVENTOR(S) : Nilsen It is certified that error appears in the above-identified patent and that said Letters Patent is hereby corrected as shown below:

Column 4, Line 31, "1a" should read --1A--.
Column 4, line 35, "1b" should read --1B--.
Column 8, line 20, cancel paragraph through line 24 and insert --(Results Not Shown)--.
Column 8, line 45, cancel paragraph through line 49.
Column 8, line 51, insert "(not shown)" after --data--.
Column 8, line 55, cancel "UP" and insert --$^{32}$P-- therefor.
Column 9, lines 16 and 17, cancel "The results are shown in FIG. 2A, and the assay is shown schematically in FIG. 2C." and insert --The assay is shown schematically in FIG. 1B. (The results are not shown.)-- therefor.
Column 9, line 18, cancel "the results of".
Column 9, lines 20 and 21, cancel "are shown in FIB. 2B (shown schematically in FIG. 2D)." and insert -- is shown schematically in FIG. 1B (results not shown). -- therefor.
Column 9, line 66, cancel "thereto" and insert -- to said oligonucleotide -- therefor.
Column 10, line 25, cancel "the".
Column 10, line 25, insert -- or amount -- after "presence".
Column 10, line 30, cancel "hybridization" and insert -- hybridized -- therefor.
Column 10, line 43, cancel both occurrences of "the".
Column 10, line 63, cancel "a" and insert -- an -- therefor.
Column 10, line 65, cancel "thereto" and insert -- to said oligonucleotide -- therefor.
Column 11, line 23, cancel "the".
Column 11, line 23, insert -- or amount -- after "presence".
Column 12, line 15, cancel "labeled".
Column 12, line 46, cancel "the".
Column 12, line 46, insert -- or amount -- after "presence".

Signed and Sealed this

Twenty-ninth Day of May, 2001

*Attest:*

NICHOLAS P. GODICI

*Attesting Officer*  *Acting Director of the United States Patent and Trademark Office*